US00PP33336P2

(12) United States Plant Patent
Geibel

(10) Patent No.: US PP33,336 P2
(45) Date of Patent: Aug. 10, 2021

(54) ***PELARGONIUM* PLANT NAMED 'PACTIOVIO'**

(50) Latin Name: ***Pelargonium* x *hortorum* X *Pelargonium peltatum***
Varietal Denomination: Pactiovio

(71) Applicant: ELSNER pac JUNGPFLANZEN GbR, Thiendorf (DE)

(72) Inventor: Martin Geibel, Dresden (DE)

(73) Assignee: Elsner pac Jungpflanzen GbR, Thiendorf (DE)

( * ) Notice: Subject to any disclaimer, the term of this patent is extended or adjusted under 35 U.S.C. 154(b) by 0 days.

(21) Appl. No.: 16/873,686

(22) Filed: Jun. 1, 2020

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./329, 324, 332
CPC ... A01H 5/02; A01H 5/00; A01H 6/42; A01H 6/425
See application file for complete search history.

(56) References Cited

PUBLICATIONS

Rudy Raes Bloemzaden NV Issuu Powerplug Cuttings—Tissue Culture 2019, retrieved on Nov. 3, 2020, retrieved from the Internet at https://issuu.com/yrr81/docs/preview_nc2017-18/14, 2 cover page, intro page, pp. 1,6-7,68-69,108-109. (Year: 2019).*
Sentier Primavera Spring 2020, retrieved on Nov. 4, 2020, retrieved from the Internet at https://sentier.it/uploads/cataloghi/catalogo_spring_P20_LOW.pdf, cover page, pp. 15,114,116. (Year: 2020).*

* cited by examiner

*Primary Examiner* — June Hwu
(74) *Attorney, Agent, or Firm* — C. Anne Whealy

(57) ABSTRACT

A new and distinct interspecific Geranium plant named 'Pactiovio', characterized by its broadly upright and mounding plant habit; vigorous growth habit; freely basal branching habit; dark green-colored leaves with a distinct zonal pattern; early and freely flowering habit; and reddish purple-colored semi-double flowers with white-colored centers that are held above the foliar plane on strong peduncles.

1 Drawing Sheet

Botanical designation: *Pelargonium* x *hortorum* X *Pelargonium peltatum.*
Cultivar denomination: 'PACTIOVIO'.

CROSS-REFERENCED TO CLOSELY-RELATED APPLICATIONS

Inventor: Martin Geibel
Applicant: Elsner pac Jungpflanzen GbR
Title: *Pelargonium* Plant Named 'Pactiopimp'
Filed: Jun. 1, 2020
Ser. No. 16/873,696

BACKGROUND OF THE INVENTION

The present invention relates to a new and distinct cultivar of interspecific Geranium plant, botanically known as *Pelargonium* x *hortorum* X *Pelargonium peltatum*, and hereinafter referred to by the cultivar name 'Pactiovio'.

The new interspecific Geranium plant is a product of a planned breeding program conducted by the Inventor in Dresden, Germany. The objective of the breeding program is to develop new vigorous interspecific Geranium plants with dark colored leaves and attractive flowers.

The new interspecific Geranium plant originated from a cross-pollination made by the Inventor in Dresden, Germany during the summer of 2016 of an unidentified proprietary selection of *Pelargonium* x *hortorum*, not patented, as the female, or seed, parent with an unidentified proprietary selection of *Pelargonium peltatum*, not patented, as the male, or pollen, parent. Seed was collected from a number of potential parent plants, combined and sown. The new interspecific Geranium plant was discovered and selected by the Inventor as a single flowering plant from within the progeny of the stated mass cross-pollination in a controlled greenhouse environment in Dresden, Germany during the spring of 2017.

Asexual reproduction of the new interspecific Geranium plant by vegetative terminal cuttings in a controlled greenhouse environment in Dresden, Germany since January, 2018 has shown that the unique features of this new interspecific Geranium plant are stable and reproduced true to type in successive generations.

SUMMARY OF THE INVENTION

Plants of the new interspecific Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pactiovio'. These characteristics in combination distinguish 'Pactiovio' as a new and distinct interspecific Geranium plant:

1. Broadly upright and mounding plant habit.
2. Vigorous growth habit.

3. Freely basal branching habit.
4. Dark green-colored leaves with a distinct zonal pattern.
5. Early and freely flowering habit.
6. Reddish purple-colored semi-double flowers with white-colored centers that are held above the foliar plane on strong peduncles.

Plants of the new interspecific Geranium can be compared to plants of the *Pelargonium* x *hortorum* 'Pactiopimp', disclosed in U.S. Plant patent application Ser. No. 16/873,696. In side-by-side comparisons, plants of the new interspecific Geranium differ from plants of 'Pactiopimp' in the following characteristics:

1. Flowers of plants of the new interspecific Geranium are semi-double types whereas flowers of plants of 'Pactiopimp' are single types.
2. Leaves of plants of the new interspecific Geranium have a more distinct zonal pattern than leaves of plants bf 'Pactiopimp'.
3. Flowers of plants of the new interspecific Geranium are darker reddish purple in color than flowers of plants of 'Pactiopimp'.

BRIEF DESCRIPTION OF THE PHOTOGRAPH

The accompanying colored photograph illustrates the overall appearance of the new interspecific Geranium plant showing the colors as true as it is reasonably possible to obtain in colored reproductions of this type. Colors in the photograph may differ slightly from the color values cited in the detailed botanical description which accurately describe the colors of the new interspecific Geranium plant.

The photograph comprises a side perspective view of a typical flowering plant of 'Pactiovio' grown in a container.

DETAILED BOTANICAL DESCRIPTION

The aforementioned photograph and following observations, measurements and values describe plants grown in 19-cm containers during the spring, summer and autumn in a glass-covered greenhouse in Dresden, Germany and under cultural practices typical of commercial interspecific Geranium production. During the production of the plants, day temperatures averaged 18° C., night temperatures averaged 16° C. and light levels ranged from 15 kilolux to 100 kilolux. Plants were four months old when the photograph was taken and nine months old when the detailed description was taken. In the detailed description, color references are made to The Royal Horticultural Society Colour Chart, 1995 Edition, except where general terms of ordinary dictionary significance are used.

Botanical classification: *Pelargonium* x *hortorum* X *Pelargonium peltatum* 'Pactiovio'.

Parentage:

*Female, or seed, parent*.—Unidentified proprietary selection of *Pelargonium* x *hortorum*, not patented.

*Male or pollen parent*.—Unidentified proprietary selection of *Pelargonium peltatum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer*.—About four weeks at temperatures about 20° C.

*Time to produce a rooted young plant, winter*.—About four weeks at temperatures about 18° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Broadly upright and mounding plant habit; broad inverted triangle; densely foliated; vigorous growth habit; rapid growth rate; freely basal branching habit with about four primary lateral branches each with about five secondary lateral branches developing per plant; pinching is typically not required.

*Plant height, to top of umbels*.—About 36 cm.

*Plant height, to top of foliar plane*.—About 34 cm.

*Plant width*.—About 50 cm.

*Lateral branches*.—Length: About 19 cm. Diameter: About 8 mm. Internode length: About 1 cm. Strength: Strong. Texture and luster: Moderately pubescent; semi-glossy. Color: Close to 146B.

Leaf description:

*Arrangement*.—Opposite and alternate; simple.

*Length*.—About 3.8 cm.

*Width*.—About 6.7 cm.

*Shape*.—Rounded to cordate.

*Apex*.—Rounded.

*Base*.—Cordate, open.

*Margin*.—Crenate.

*Venation pattern*.—Palmate.

*Texture and luster, upper and lower surfaces*.—Pubescent; coriaceous; matte.

*Color*.—Developing and fully expanded leaves, upper surface: Close to 147A; zonal pattern, medium in conspicuousness and size, located in the center of the leaf, darker than 147A; venation, close to 147A. Developing and fully expanded leaves, lower surface: Close to 147B; venation, close to 144A.

*Petioles*.—Length: About 6 cm. Diameter: About 2 mm. Strength: Moderately strong. Texture and luster, upper and lower surfaces; Pubescent; semi-glossy. Color, upper and lower surfaces: Close to 147B.

Flower description:

*Flower arrangement and flowering habit*.—Semi-double flowers arranged in hemispherical umbels arising from apical leaf axils; umbels displayed above the foliar plane on strong peduncles; flowers face upright to outwardly depending on the position on the umbel; freely flowering habit with about seven open flowers per umbel and numerous umbels developing per plant during the flowering season.

*Fragrance*.—None detected.

*Flowering season*.—Early flowering habit; plants begin flowering about 70 days after planting; in the garden in Germany, flowering begins in April and continues until frost in the autumn.

*Flower longevity*.—Flowers last about six to ten days on the plant; umbels last about three to four weeks on the plant; flowers persistent.

*Umbel height*.—About 5 cm.

*Umbel diameter*.—About 10 cm.

*Flower diameter*.—About 5.5 cm.

*Flower depth* (*height*).—About 2 cm.

*Flower buds*.—Length: About 8 mm. Diameter: About 6 mm. Shape: Rounded to elliptic. Texture and luster: Pubescent; matte. Color: Close to 144A.

*Petals*.—Quantity per flower: About nine; petals slightly imbricate. Length, upper petals: About 3 cm. Length, lower petals: About 2.8 cm. Width, upper petals: About 1.9 cm. Width, lower petals: About 2.2 cm. Shape: Obovate. Apex: Rounded. Base: Cuneate. Margin: Entire; slightly undulate. Texture and luster, upper and lower surfaces: Smooth, glabrous; glossy. Color: When opening and fully opened, upper surface: Close to between 66A and 74A; towards the base, close to 155D; venation, faint, stripes, close to between 66A and 74A; color becoming closer to 66A with development. When opening and fully opened, lower surface: Close to 66C; venation, close to 66A; color does not change with development.

*Petaloids*.—To date, petaloid development has not been observed on plants of the new interspecific Geranium.

*Sepals*.—Quantity per flower: Five arranged in a single whorl. Length: About 1.2 cm. Width: About 3 mm to 4 mm. Shape: Lanceolate; not reflexing. Apex: Acute. Base: Truncate. Margin: Entire. Texture and luster, upper surface: Smooth, glabrous; glossy. Texture and luster, lower surface: Pubescent; semi-glossy. Color, upper and lower surfaces: Close to 146A; towards the base, close to 166A.

*Peduncles* (*umbel stems*).—Length: About 12 cm. Diameter: About 4 mm. Strength: Strong; flexible. Angle: Mostly upright. Texture and luster: Pubescent; semi-glossy. Color: Close to 144A.

*Pedicels* (*individual flower stems*).—Length: About 2.5 cm. Diameter: About 1 mm. Strength: Moderately strong; flexible; no swelling observed. Texture and luster: Pubescent; semi-glossy. Color: Close to 166A.

*Reproductive organs*.—Androecium: Stamen quantity per flower: About twelve. Filament length: About 4 mm. Filament color: Close to 155D. Anther size: About 1 mm by 2 mm. Anther shape: Tubular. Anther color: Close to 66A. Pollen amount: Abundant. Pollen color: Close to 167A. Gynoecium: Pistil quantity per flower: One. Pistil length: About 8 mm. Stigma diameter: About 3 mm. Stigma shape: Five-parted. Stigma color: Close to 58B. Style length: About 3 mm. Style color: Close to 58B. Ovary color: Close to 139D. Seeds and fruits: To date, seed and fruit development have not been observed on plants of the new interspecific Geranium.

Pathogen & pest resistance: To date, plants of the new interspecific Geranium have not been observed to be resistant to pathogens and pests common to interspecific Geraniums.

Temperature tolerance: Plants of the new interspecific Geranium have been observed to tolerate temperatures ranging from about 0.5° C. to about 40° C.

It is claimed:

1. A new and distinct interspecific Geranium plant named 'Pactiovio' as illustrated and described.

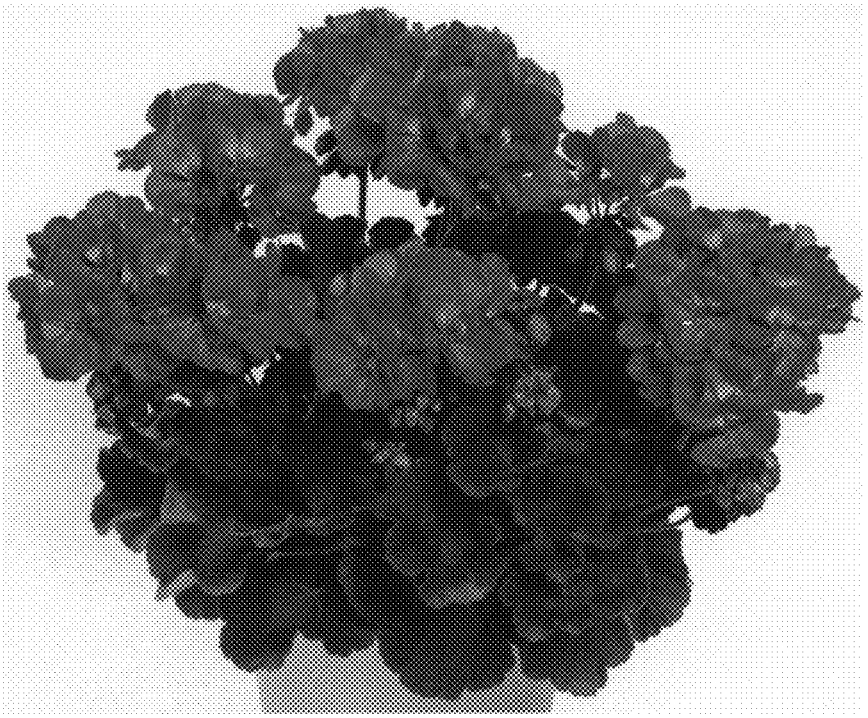

* * * * *